(12) United States Patent
Jayaraman et al.

(10) Patent No.: US 11,603,561 B2
(45) Date of Patent: Mar. 14, 2023

(54) METHOD FOR DIRECT QUANTIFICATION OF NUCLEIC ACIDS IN REAL TIME QPCR

(71) Applicant: INDIAN INSTITUTE OF TECHNOLOGY MADRAS (IIT MADRAS), Chennai (IN)

(72) Inventors: Guhan Jayaraman, Chennai (IN); Sudeshna Sengupta, Chennai (IN); Shivansh Goyal, Chennai (IN)

(73) Assignee: INDIAN INSTITUTE OF TECHNOLOGY MADRAS (IIT MADRAS), Chennai (IN)

( * ) Notice: Subject to any disclaimer, the term of this patent is extended or adjusted under 35 U.S.C. 154(b) by 65 days.

(21) Appl. No.: 16/766,205

(22) PCT Filed: Nov. 30, 2018

(86) PCT No.: PCT/IN2018/000054
§ 371 (c)(1),
(2) Date: May 21, 2020

(87) PCT Pub. No.: WO2019/106684
PCT Pub. Date: Jun. 6, 2019

(65) Prior Publication Data
US 2020/0377934 A1    Dec. 3, 2020

(30) Foreign Application Priority Data
Nov. 30, 2017   (IN) .............................. 201741042960

(51) Int. Cl.
*C12Q 1/6851*   (2018.01)
*C12Q 1/686*    (2018.01)

(52) U.S. Cl.
CPC ........... *C12Q 1/6851* (2013.01); *C12Q 1/686* (2013.01); *C12Q 2521/301* (2013.01);
(Continued)

(58) Field of Classification Search
CPC ............ C12Q 2525/205; C12Q 1/6851; C12Q 2563/107; C12Q 2521/301;
(Continued)

(56) References Cited

U.S. PATENT DOCUMENTS 9,580,749 B2    2/2017 Mao et al.
2017/0191120 A1 7/2017 Morrison
2017/0226576 A1 8/2017 Caplin

FOREIGN PATENT DOCUMENTS

WO    2021086604 A1   5/2021

OTHER PUBLICATIONS

Sando et al., "Light-Up Hoechst-DNA Aptamer Pair: Generation of an Aptamer-Selective Fluorophore from a Conventional DNA-Staining Dye," ChemBioChem, vol. 8, pp. 1795-1803. (Year: 2007).*
(Continued)

*Primary Examiner* — Young J Kim
(74) *Attorney, Agent, or Firm* — Troutman Pepper Hamilton Sanders LLP

(57) ABSTRACT

A method for direct quantification of nucleic acids in real time qPCR. The invention discloses a method for specific quantification of nucleic acids in real time qPCR. The disclosed invention can be achieved in three ways; 1) using a modified primer for qPCR quantification; 2) using strand displacement based probes for qPCR quantification; 3) using label-free endonuclease probe for qPCR quantification. The mechanism of quantification is based on the fact that, DNA, RNA or modified oligonucleotide based light-up dye-aptamer system, where dye is not fluorescent in free state but its fluorescence increases multi-fold when it binds to its specific aptamer.

3 Claims, 3 Drawing Sheets

Specification includes a Sequence Listing.

(52) U.S. Cl.
CPC .......... *C12Q 2525/205* (2013.01); *C12Q 2537/1376* (2013.01); *C12Q 2537/163* (2013.01); *C12Q 2561/113* (2013.01); *C12Q 2563/107* (2013.01)

(58) Field of Classification Search
CPC ...... C12Q 2537/1376; C12Q 2537/163; C12Q 1/686; C12Q 2561/113
See application file for complete search history.

(56) References Cited

OTHER PUBLICATIONS

Yang et al., "Real-time PCR detection of protein analytes with conformation-switching aptamers," Analytical Biochemistry, vol. 380, pp. 164-173. (Year: 2008).*

Ouellet, Jonathan, "RNA Flourescence with Light-up Aptamers," Frontiers in Chemistry, June, vol. 4, No. 29, pp. 1-12. (Year: 2016).*

Gasparic et al. 2008. Comparison of different real-time PCR chemistries and their suitability for detection and quantification of genetically modified organisms, BMC Biotechnology, 8 (26): 1-12; Mar. 6, 2008 Abstract and first full paragraph in the right column on p. 2. https://pubmed.ncbi.nlm.nih.gov/20087729/, Abstract Only.

International Search Report and Written Opinion of International Searching Authority for PCT/IN2018/000054, ISA/IN, Dwarka, New Delhi, dated Mar. 15, 2019.

Kutyavin, IV. 2010. New approach to real-time nucleic acids detection: folding polymerase chain reaction amplicons into a secondary structure to improve cleavage of Fo •• rster resonance energy transfer probes in 5'-nuclease assays, Nucleic Acids Research, 38 (5): e29; Published online: Dec. 7, 2009 The Whole Document. https://pubmed.ncbi.nlm.nih.gov/19969535/.

Navarro et al. 2015. Real-time PCR detection chemistry, Clinica Chimica Acta, 439:231-50; Jan. 15, 2015 The Whole Document https://www.sciencedirect.com/science/article/abs/pii/S0009898114004483.

Sando et al. 2007. Light-Up Hoechst-DNA Aptamer Pair: Generation of an Aptamer-Selective Fluorophore from a Conventional DNA-Staining Dye, ChemBioChem, 8 (15), 1795-1803; Oct. 15, 2007 www.researchgate.net/publication/6034625_Light-Up_Hoechst-DNA_Aptamer_Pair_Generation_of_an_Aptamer-Selective_Fluorophore_from_a_Conventional_DNA-Staining_Dye.

\* cited by examiner

METHOD FOR DIRECT QUANTIFICATION OF NUCLEIC ACIDS IN REAL TIME QPCR

CROSS-REFERENCE TO RELATED APPLICATIONS

This application is a U.S. National Stage application under 35 USC 371 of International application number PCT/IN2018/000054, filed on Nov. 30, 2018, which claims priority to Indian application number IN201741042960, filed on Nov. 30, 2017, the contents of which are hereby incorporated by reference in their entirety.

The instant application contains a Sequence Listing which has been submitted in ASCII format via EFS-Web and is hereby incorporated by reference in its entirety. Said ASCII copy, is named 259464_000004_SL.txt, having a file size of 761 bytes, and created Jan. 10, 2023.

TECHNICAL FIELD

Embodiments are generally related to the field of quantification of nucleic acids using label-free biosensors. Embodiments are further related to direct quantification of DNA amplification in real time qPCR using light up dye-DNA/RNA aptamer pair.

BACKGROUND OF THE INVENTION

Real time quantitative PCR (qPCR) is a robust technique, extensively used in biological research for studying mRNA expression, DNA copy number, allele variations etc. (Arya et al. 2005). It has revolutionized diagnostics, offering fast, sensitive and specific detection of diseases such as Dengue, Influenza A and B, Zika etc. (Arya et al. 2005). qPCR uses two basic chemistries for quantification of amplicons: One uses non-sequence-specific, dsDNA binding fluorogenic dyes, such as EtBr and SYBR Green 1, which are cost effective but have lower specificity(Arya et al. 2005). The other method involves fluorescent probes (FP) such as molecular beacons, TaqMan, Scorpions etc., which use sequence-specific oligonucleotides (Marras, Tyagi, and Kramer 2006). These FRET (fluorescence resonance energy transfer) based probes are expensive due to the chemical modifications of oligonucleotide's required for attaching the fluorophore and the quencher, but successfully prevent non-specific amplification of the target (Arya et al. 2005).

Hence, there is an urgent need to develop cost effective alternative method without any compromise on specificity for fully exploiting the potential of qPCR. There has been development of alternative technologies based on microarray and next-generation sequencing to overcome the limitations of PCR based methods, but these also have their own limitations (Khodakov, Wang, and Zhang 2016). Thus, the present invention is a method to develop an economically feasible sequence specific probe for applications in qPCR for DNA amplification.

SUMMARY OF THE INVENTION

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

Therefore, one aspect of the disclosed embodiment is to provide a method using a modified primer for qPCR quantification of nucleic acids.

Another aspect of the disclosed embodiment is to provide a method using strand displacement based probes for qPCR quantification of nucleic acids.

Further aspect of the disclosed embodiment is to provide a method using label-free endonuclease probe for qPCR quantification of nucleic acids.

The aforementioned aspects and other objectives and advantages can now be achieved as described herein. A simple and shorter Aptamer-based qPCR (Apt-qPCR) probe is used for quantification in real-time PCR wherein the probe uses a light-up dye-aptamer system in which the dye shows negligible fluorescence in the free-state and its fluorescence increases manifold when it binds to its specific aptamer. In the method using modified primer for qPCR quantification, there is an aptamer upstream of one or both of the designed primer oligos. This primer initially in the pre-annealed form will show fluorescence as aptamer is free and single stranded and can bind to the dye. However, following primer's annealing and extension step of the PCR, the aptamer will become double stranded, thus losing its 3D structure which is required for binding to the dye. This double stranded DNA is not specific for the dyes and will not bind to it. Therefore one free aptamer is lost for each primer that gets consumed in PCR reaction giving specific and accurate PCR quantification through exponential decrease in fluorescence.

In the method using label-free strand displacement based probes, there is a sequence complementary to an aptamer upstream of one or both the primers. This sequence binds to aptamer and makes it double stranded. This will prevent aptamer from binding to its ligand dye present in the solution. During the PCR, this probe will go and anneal to its target. Thermally stable polymerase with no 5'-3' exonuclease activity and high strand displacement properties will be used for the PCR reaction with ability to extend from nicks in the double helix. This polymerase during the extension step of the PCR will displace the aptamer and make its complementary sequence double stranded. Therefore one free aptamer will be released for each primer that is used in the PCR reaction therefore giving highly specific and accurate PCR quantification. This released aptamer can even be combined with downstream applications for signal generation or in DNA nanotechnology or DNA/RNA circuit based reactions.

In method using label-free endonuclease probe for qPCR quantification, a label-free endonuclease probe is presented having a blocked aptamer at its 5' end, such that inhibitor region of probe prevents aptamer from binding to the fluorophore. During the annealing step of the PCR, the probe will go and bind sequence-specifically to its target like Taqman probe and the DNA aptamer and blocker will get physically separated. The aptamer will get released during the extension step of the PCR with the help of 5'-flap endonuclease activity of DNA polymerase enzyme. This will lead to accumulation of the aptamer corresponding to each extension step thus quantifying DNA amplification. An environment-sensitive fluorophore will specifically bind to the released aptamer, enhancing the fluorescence by 50-700-fold depending on the dye-aptamer system used and this fluorescence can be measured at the end of each cycle at appropriate temperature. This method will provide sequence-specific real-time amplicon quantitation with no post-PCR processing at a cheaper price compared to Taqman probes. They will also have the capability of multiplexing which is one of the major disadvantages of SYBR Green.

The method disclosed herein is specific and cost effective method for DNA quantification in real time qPCR. The amplicon detection is sequence specific without involving modified oligonucleotides, thereby reducing the cost, compared to fluorescent probes.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
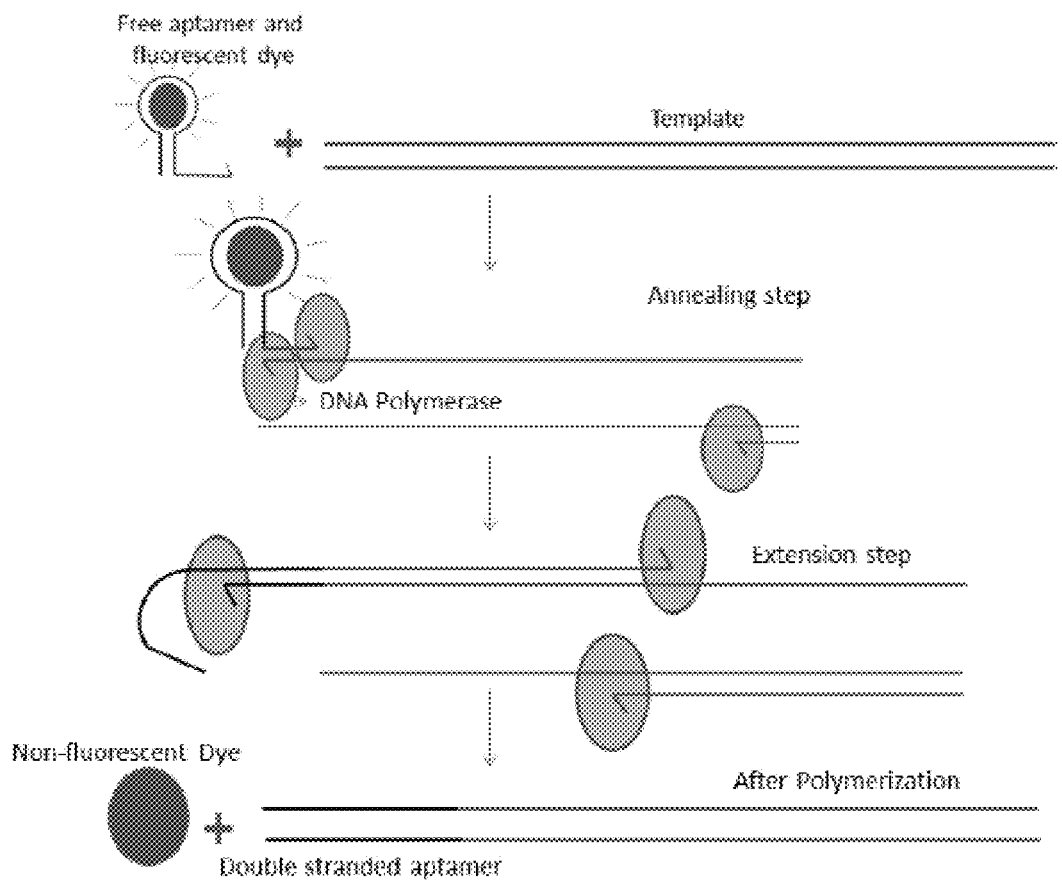
FIG. 1 illustrates a schematic representation of mechanism of action of quantification of nucleic acids using a modified primer.

FIG. 1 illustrates a schematic representation 100 of mechanism of action of quantification of nucleic acids using a modified primer. A simple and shorter Aptamer-based qPCR (Apt-qPCR) probe is used for quantification in real-time PCR wherein the probe uses a light-up dye-aptamer system in which the dye shows negligible fluorescence in the free-state and its fluorescence increases manifold when it binds to its specific aptamer. In the method using modified primer for qPCR quantification, we have an aptamer upstream of one or both of the designed primer oligo. This primer initially in the pre-annealed form will show fluorescence as aptamer is free and single stranded and can bind to the dye, as shown at FIG. 1. However, following primer's annealing and extension step of the PCR, the aptamer will become double stranded, thus losing its 3D structure which is required for binding to the dye. This double stranded DNA is not specific for the dyes and will not bind to it. Therefore one free aptamer is lost for each primer that gets consumed in PCR reaction giving specific and accurate PCR quantification through exponential decrease in fluorescence. Note that L-Asparaginase gene (ansB) and UDP-glucose 6-dehydrogenase (hasB) were used as templates for qPCR.

Figure 2:
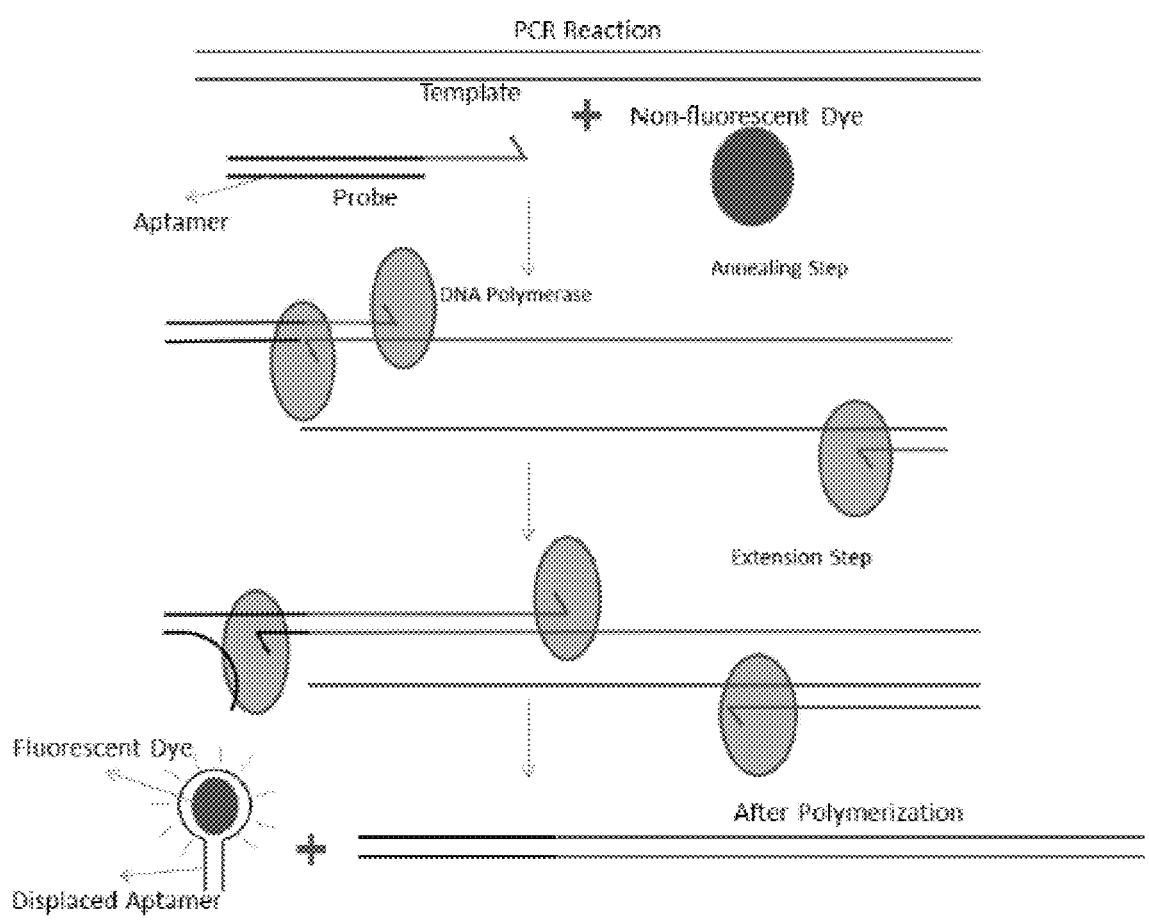
FIG. 2 illustrates a schematic representation of mechanism of action of quantification of nucleic acids using a strand displacement based probes.

FIG. 2 illustrates a schematic representation 200 of mechanism of action of quantification of nucleic acids using a strand displacement based probes. In the method using label-free strand displacement based probes, there is a sequence complementary to an aptamer, upstream of one or both the primers. This sequence binds to aptamer and makes it double stranded. This will prevent aptamer from binding to its ligand dye present in the solution. During the PCR, this probe will go and anneal to its target, as shown in FIG. 2. Thermally stable polymerase with no 5'-3' exonuclease activity and high strand displacement properties will be used for the PCR reaction with ability to extend from nicks in the double helix. This polymerase during the extension step of the PCR will displace the aptamer and make its complementary sequence double stranded. Therefore one free aptamer will be released for each primer that is used in the PCR reaction therefore giving highly specific and accurate PCR quantification. This released aptamer can even be combined with downstream applications for signal generation or in DNA nanotechnology or DNA/RNA circuit based reactions.

The fluorescence enhancement was measured for dye and aptamer (1:1 concentration) where both have concentrations of 1 µM in various solvents with 15 mins of incubation, unless and otherwise the reaction conditions are specified. Fon/Foff was used to analyze fluorescence enhancement and is calculated as ratio of fluorescence of dye when bound to aptamer divided by the fluorescence observed when the only dye is present in the reaction.

Figure 3:
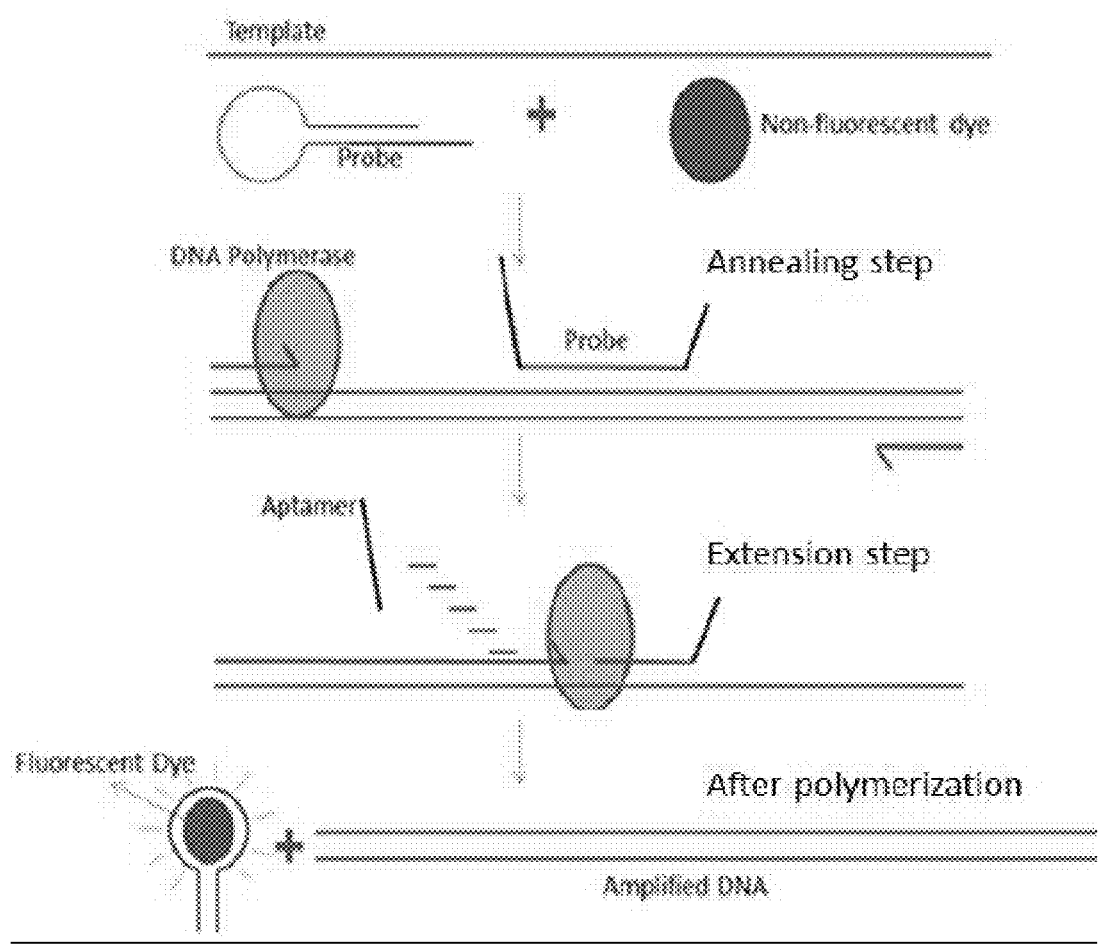
FIG. 3 illustrates a schematic representation of mechanism of action of quantification of nucleic acids using label free endonuclease based probes.

FIG. 3 illustrates a schematic representation 300 of mechanism of action of quantification of nucleic acids using label free endonuclease based probes. In method using label-free endonuclease probe for qPCR quantification, a label-free endonuclease probe is presented having a blocked aptamer at its 5' end, such that inhibitor region of probe prevents aptamer from binding to the fluorophore. During the annealing step of the PCR, the probe will bind sequence-specifically to its target like Taqman probe and the DNA aptamer and blocker will get physically separated (FIG. 3). The aptamer will get released during the extension step of the PCR with the help of 5'-flap endonuclease activity of the DNA polymerase enzyme. This will lead to accumulation of the aptamer corresponding to each extension step thus quantifying DNA amplification. An environment-sensitive fluorophore will specifically bind to the released aptamer, enhancing the fluorescence by 50-700-fold depending on the dye-aptamer system used and this fluorescence can be measured at the end of each cycle at appropriate temperature. This method will provide sequence-specific real-time amplicon quantitation with no post-PCR processing at a cheaper price compared to Taqman probes. They will also have the capability of multiplexing which is one of the major disadvantages of SYBR Green.

The method disclosed herein is specific and cost effective method for DNA quantification in real time qPCR. The amplicon detection is sequence specific without involving chemically modified oligonucleotides, thereby reducing the cost, compared to fluorescent probes.

hasB primers were optimized for the reaction using gradient PCR. Reaction conditions for the gradient PCR with Taq PCR kit are: 95° C. for 5 min, followed by 30 cycles of denaturation for 20 sec at 95° C., annealing at 56/57.7/60.1/62° C. for 20 sec and extension at 68° C. for 25 sec, and a final extension at 68° C. for 2 min. For the above reaction 200 nM of primers, 200 nM of dNTPs, 400 nM of DIR, 5.91 ng/20 µL hasB template and 0.5 units of Taq DNA polymerase were used in a 20 µL reaction.

Standard Taq PCR kit with DIR (Apt-qPCR) and standard Sybr Green qPCR kit was used for qPCR amplification of hasB gene. Reverse Primer has DIR aptamer in 5' upstream direction for reporting the decrease in signal. Standards of 10 ng/20 µL, 1 ng/20 µL, 0.1 ng/20 µL, 0.01 ng/20 µL and 0.001 ng/20 µL plasmid concentration were PCR amplified with a no template control. Analysis of PCR assays using Sybr Green kit was done using QuantStudio Dx software. For standard curve in the DIR based qPCR, an arbitrary threshold in the linear region of the exponential decrease in fluorescence is defined to find fractional Ct values which are then plotted against log(amount of initial DNA).

Reaction conditions for hasB with Taq polymerase are 95° C. for 5 min, followed by 32 cycles of denaturation at 95° C. for 15 sec, annealing at 60° C. for 20 sec, extension at 68° C. for 25 sec and fluorescence measurement at 25° C. for 25 sec. For the above reaction 200 nM of primers, 200 nM of dNTPs, 400 nM of DIR and 0.45 units of Taq polymerase were used in a 18 µL reaction. Reaction conditions for hasB with Dynamo SYBR Colour Flash kit are 95° C. for 7 min, followed by 40 cycles of denaturation at 95° C. for 10 sec and a combined annealing and extension step at 60° C. for 25 sec.

Sequences of primers used were as following:

```
Forward Primer:
                                        (SEQ ID NO: 1)
    5'-atgggctcacaggaggctgag-3'

Reverse Primer:
                                        (SEQ ID NO: 2)
gacgacgacgctaggaaggcgttggtgggcacgccggtcgtccctttggc
aggcaatagccgc-3'
```

Standard Phusion hf PCR kit with DIR was used to PCR amplify the segment of hasB gene with same primers used above. Standards of 10 ng/20 µL, 2 ng/20 µL, 0.4 ng/20 µL, 0.08 ng/20 µL and 0.016 ng/20 µL plasmid concentration were PCR amplified with a no template control (NTC). A standard curve was plotted in a similar method as described for amplification with Taq polymerase in Section 3.6. Reaction conditions for qPCR of hasB gene with Phusion hf polymerase are 98° C. for 3 min, followed by 30 cycles of denaturation at 98° C. for 10 sec, a combined annealing and extension step at 72° C. for 20 sec and fluorescence measurement at 25° C. for 20 sec. For the above reaction 500 nM of primers, 200 nM of dNTPs, 750 nM of DIR and 0.36 units of Phusion hf polymerase were used in a 18 µL reaction.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for direct quantification of nucleic acids in real time qPCR using a dye aptamer system, said method comprising:
    forming a dye aptamer system by placing the aptamer 5' upstream of one or both primers, wherein the aptamer is free and single-stranded to bind to the dye and fluoresce;
    performing annealing and extension step, wherein the dye bound dye aptamer system is annealed to a strand of target nucleic acid and extended;
    releasing the dye by annealing the reverse primer with the extension product of the dye bound aptamer, wherein the aptamer becomes double stranded losing its 3D structure of the dye aptamer system and wherein the dye in the free state shows negligible fluorescence and the reduction in fluorescence of the solution is measured corresponding to each cycle of the PCR reaction; and
    quantifying nucleic acids in real time.

2. The method of claim 1, further comprising: monitoring an exponential decrease in fluorescence corresponding to a consumption of the primers with an exponential increase in an amount of DNA during PCR reaction.

3. The method of claim 1, wherein the double stranded aptamer forms a double helix to prevent the aptamer from binding to the dye in its free state present in the solution.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic-Forward Primer

<400> SEQUENCE: 1
atgggctcac aggaggctga g                                        21

<210> SEQ ID NO 2
<211> LENGTH: 63
<212> TYPE: DNA
<213> ORGANISM: Artificial Sequence
<220> FEATURE:
<223> OTHER INFORMATION: Synthetic -Reverse Primer

<400> SEQUENCE: 2
gacgacgacg ctaggaaggc gttggtgggc acgccggtcg tccctttggc aggcaatagc   60
cgc                                                               63
```